United States Patent [19]

Bradford et al.

[11] Patent Number: Plant 6,363

[45] Date of Patent: Nov. 1, 1988

[54] NECTARINE TREE (AUGUST RED)

[76] Inventors: Norman G. Bradford, 11875 E. Savana Rd.; Lowell G. Bradford, 12439 E. Savana Rd., both of Le Grand, Calif. 95333

[21] Appl. No.: 46,775

[22] Filed: May 7, 1987

[51] Int. Cl.[4] ..... A01H 5/03

[52] U.S. Cl. ..... Plt./41

[58] Field of Search ..... Plt./41

*Primary Examiner*—Robert E. Bagwill

[57] ABSTRACT

The present invention relates to a clingstone nectarine tree and more particularly to a new and distinct variety broadly characterized by a medium size, vigorous, very productive and regular bearing tree, the fruit of which ripens approximately the last week of August. The variety has a more exceptional red blush skin coloring at picking time than most other late varieties and is of outstanding firmness. This extreme firmness allows for an extended harvest period with more opportunity for the grower to consider market developments before picking. The variety was developed from a second generation seedling of a cross of Red Diamond (U.S. Plant Pat. No. 3,165) seed parent by Autumn Free (U.S. Plant Pat. No. 2,976) pollen parent. The original seedling was transplanted in 1981 and has been asexually reproduced by budding and grafting, and such reproduction of plant and fruit characteristics were true to the original plant in all respects.

1 Drawing Sheet

BACKGROUND OF THE VARIETY

The present variety of nectarine tree was produced by us at Bradford Farms in Merced County (San Joaquin Valley), Calif., as the result of a seedling of an open pollinated unnamed seedling. This unnamed seedling originated from the selected seed parent, Red Diamond (U.S. Plant Pat. No. 3,165), being crossed by the selected pollen parent, Autumn Free (U.S. Plant Pat. No. 2,976). Subsequent to origination of the present variety of nectarine tree, we asexually reproduced it by budding and grafting, and such reproduction of plant and fruit characteristics were true to the original plant in all respects.

The present variety most nearly resembles Autumn Grand (U.S. Plant Pat. No. 2,894), but is distinguished from and an improvement on that variety and other known late maturing varieties in having fruit which is firmer, has better red color in our area, and which first ripens 3 days before Autumn Grand, but has an extended harvest period because of its extreme firmness. The fruit is further distinguished by average size, good acidic flavor, and excellent shape for the commercial grower.

This present variety differs substantially from Red Diamond (U.S. Plant Pat. No. 3,165) by ripening approximately 60 days later and by being a clingstone rather than a freestone. It also substantially differs from its other grandparent, Autumn Free (U.S. Plant Pat. No. 3,165) by being a clingstone instead of a freestone, by having much superior red color, and by ripening 5 days later.

DRAWING

The accompanying photograph shows the characteristics of the whole fruit in skin color and form, a characteristic fruit divided on its suture plane showing the flesh and stone, and typical leaves.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of hard ripe on Sept. 5, 1985. All major color code designations are by reference to the Inter-Society Color Council, National Bureau of Standards. Common color names are also used occasionally.

TREE

Size: Medium.
Vigor: Vigorous.
Growth: Upright and dense.
Form: Vase-shaped.
Hardiness: Hardy.
Production: Productive.
Bearing: Regular bearer.
Trunk:
- *Size.*—Medium.
- *Texture.*—Medium.
- *Color.*—Brownish gray, [64 brGy].
- *Lenticels.*—Numerous, large. Color: Light yellowish brown [76 l.yBr]. Size: $\frac{3}{8}''$ to $\frac{1}{2}''$, [9.535–12.713 mm.].

Branches:
- *Size.*—Medium.
- *Texture.*—Medium.
- *Color.*—1st Year wood — Topside: Deep reddish brown [41 deep rBr]. 1st Year wood — Underside: Moderate yellow green [120 m.YG]. Older wood: Grayish reddish brown [46 gy.rBr].
- *Lenticels.*—Numerous, medium. Color: Light yellowish brown [76 l.yBr]. Average size: $\frac{1}{4}''$ [6.356 mm.].

Leaves:
- *Size.*—Medium. Average length: 5" [127 mm.]. Average width: $1\frac{1}{2}''$ [38.1 mm.].
- *Thickness.*—Medium.
- *Form.*—Lanceolate.
- *Apex.*—Acuminate.
- *Base.*—Acute.
- *Surface.*—Smooth.

*Color.*—Dorsal surface: Dark yellowish green [137 d.yG]. Ventral surface: Deep yellow green [118 deep YG].

*Margin.*—Crenate.

*Venation.*—Pinnately net veined.

*Petiole.*—Medium length and thickness. Average length: ½" [12.7 mm.]. Average thickness: 1/16" [1.587 mm.].

*Glands.*—Numbers: Mostly 2, 3 or 4 per leaf. Position: Some alternately and some oppositely positioned on petiole and base of blade. Size: Medium. Form: Reniform. Color: Brilliant yellow green [116 brill.YG].

*Stipules.*—Few in number. Length: ⅛" to ¼" [3.175-6.35 mm.].

Flower buds:

*Hardiness.*—Hardy.

*Size.*—Medium.

*Length.*—Medium.

*Form.*—Free.

*Surface.*—Pubescent.

Flowers:

*Blooming period.*—Medium, as compared with other varieties.

*Size.*—Small.

*Color.*—Pale pink [7 p.Pk].

FRUIT

Maturity when described: Hard ripe, Sept. 5, 1985.

Date of first picking: Aug. 28, 1985.

Date of last picking: Sept. 9, 1985.

Size: Uniform, medium.

*Average diameter axially.*—2⅜ "[60.33 mm].

*Average traversely in suture plane.*—2⅜" [60.33 mm].

Form: Uniform, globose, symmetrical, but having a slightly higher lip along one side of the suture.

*Longitudinal section form.*—Circular.

*Transverse section through diameter.*—Circular.

Suture: An inconspicuous line extending from the base, discontinuing at the apex, and having a marked depression only at the pistil point.

Ventral surface: Rounded slightly, slightly lipped throughout on left side.

Lips: A slight lip occurs only on one side.

Cavity: Flaring, circular, suture showing only on one side.

Base: Rounded, short stem causes characteristic stem marks on some fruit.

Apex: Short, of negligible length, depressed.

Pistil point: Slightly oblique on most mature fruits.

Stem: Short.

*Average length.*—⅜" [9.525 mm.].

*Average width.*—3/16" [4.762 mm.].

Skin:

*Thickness.*—Medium.

*Texture.*—Medium.

*Tenacity.*—Tenacious to flesh.

*Tendency to crack.*—None observed as of yet.

*Color.*—Deep red [13 deep R] streaks with deep reddish orange [36 deep rO] to light yellow [86 l.Y] background.

Flesh:

*Color.*—Light yellow [86 l.Y] with very deep red [14 v.deep R] appearing only very close to the pit.

*Amygdalin.*—Abundant.

*Juice.*—Moderate.

*Texture.*—Very firm, very crisp, fine.

*Fibers.*—Abundant, fine, tender.

*Ripens.*—Mostly even, but slightly earlier at base.

*Flavor.*—Acidic.

*Aroma.*—Very slight.

*Eating quality.*—Good, and improves during cold storage.

STONE

Type: Clingstone.

Form: Oval.

Base: Straight.

Apex: Acute.

Sides: Unequal, curved on right side.

Surface: Irregularly furrowed throughout with pitting toward base.

Ridges: Jagged.

Color: Dried pit appears light brown [57 l.Br].

Pit wall: 3/16" to ¼" [4.762-6.35 mm.] thick.

Tendency to split: Very slight, with none observed as of yet.

Kernel:

*Form.*—Oval.

*Taste.*—Bitter.

*Viable.*—Yes.

*Average width.*—½" [12.7 mm.].

*Average length.*—11/16" [17.462 mm.].

Pellicle:

*Color.*—Moderate brown [58 m.Br].

Amygdalin: Abundant.

USE

Market: Fresh and long distance shipping.

Keeping quality: Good to excellent.

Shipping quality: Good to excellent.

Resistance to insects: No unusual susceptibilities noted.

Resistance to diseases: Somewhat susceptible to brown-rot on wet years.

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct late ripening variety of clingstone nectarine tree, substantially as illustrated and described, which most nearly resembles the Autumn Grand (U.S. Plant Pat. No. 2,894) variety but is distinguished from and an improvement on that variety and other known late maturing varieties in having fruit which is firmer, has better red color in our area, and which first ripens 3 days before Autumn Grand but has an extended harvest period because of its extreme firmness, the fruit having average size, good flavor, and excellent shape for the commercial grower.

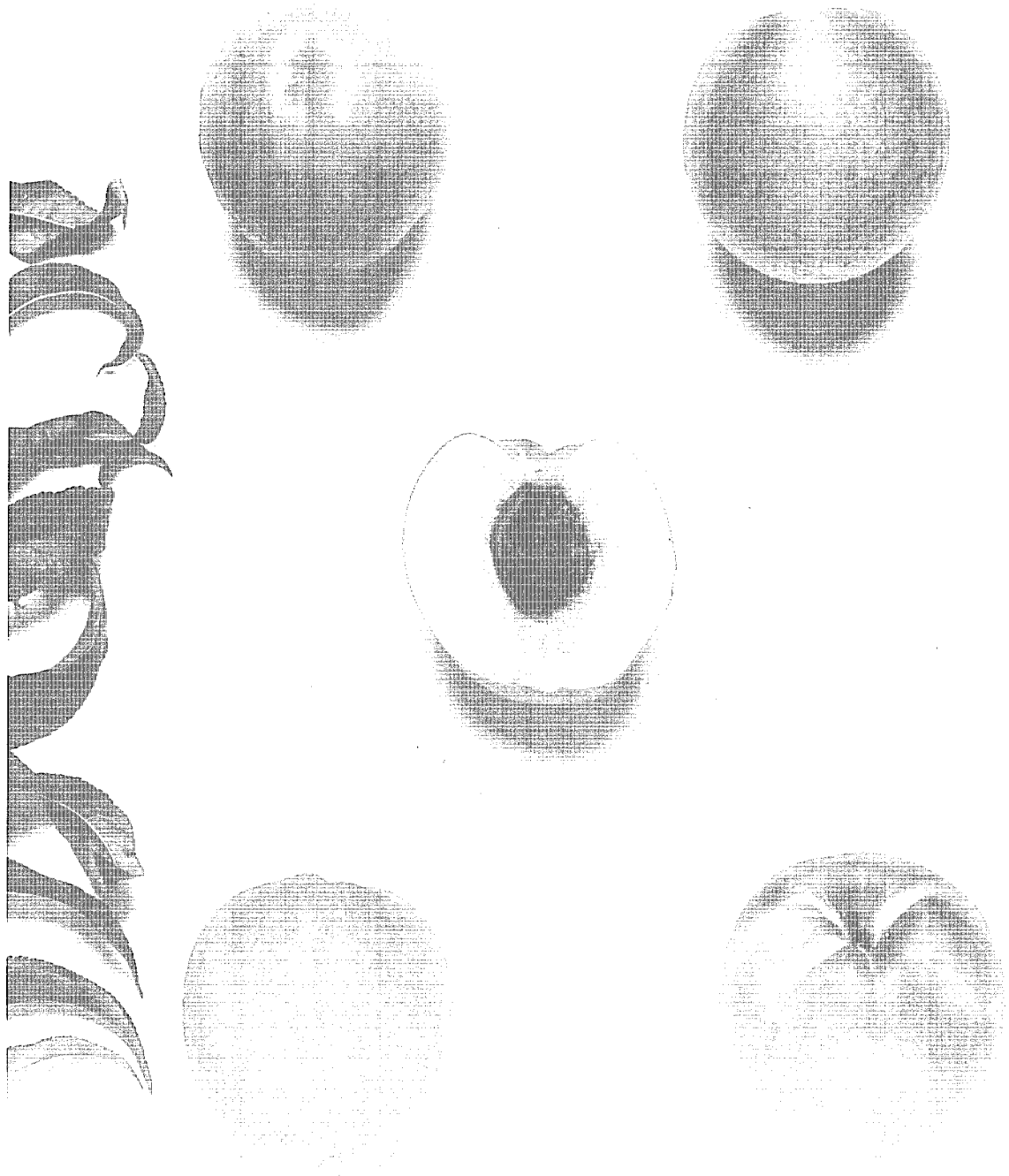

* * * * *